United States Patent [19]
Neftel et al.

[11] Patent Number: 5,968,014
[45] Date of Patent: Oct. 19, 1999

[54] CONTINUOUSLY OPERATING INFUSION DEVICE AND METHOD

[75] Inventors: Frédéric Neftel, Lausanne, Switzerland; Bernard Bouvier, Eragny sur Oise, France

[73] Assignee: DEBIOTECH S.A., Lausanne, Switzerland

[21] Appl. No.: 09/029,130

[22] PCT Filed: Aug. 20, 1996

[86] PCT No.: PCT/FR96/01297

§ 371 Date: Feb. 24, 1998

§ 102(e) Date: Feb. 24, 1998

[87] PCT Pub. No.: WO97/07842

PCT Pub. Date: Mar. 6, 1997

[30] Foreign Application Priority Data

Aug. 25, 1995 [FR] France .................................. 95 10094

[51] Int. Cl.⁶ ................................................ A61M 1/00
[52] U.S. Cl. ........................................ 604/151; 604/131
[58] Field of Search ..................... 604/131, 151, 604/80, 191, 284, 410, 122, 153, 154

[56] References Cited

U.S. PATENT DOCUMENTS 4,395,260   7/1983   Todd et al. ............................... 604/122
5,322,500   6/1994   Johnson et al. ........................... 604/4
5,328,463   7/1994   Barton et al. .

FOREIGN PATENT DOCUMENTS

| 0 473 240 A2 | 3/1992 | European Pat. Off. . |
| 0 650 739 A1 | 5/1995 | European Pat. Off. . |
| 43 33 266 A1 | 3/1995 | Germany . |
| WO 92/11881 | 7/1992 | WIPO . |

*Primary Examiner*—Corrine McDermott
*Assistant Examiner*—Cris L. Rodriguez
*Attorney, Agent, or Firm*—Wolf, Greenfield Sacks, P.C.

[57] ABSTRACT

The invention relates to injection apparatus that is capable of operating continuously. According to the invention, the apparatus comprises two independent injection bottles (12) of at least one liquid that is to be injected into a patient via a tube, each of the bottles including means (51) for detecting that injection of the liquid contained in the bottle has terminated, which means control means (53) for interrupting the flow of liquid. The apparatus comprises upstream injection apparatus (10) having two feeder tubes (50) connected to respective bottles (12), and downstream injection apparatus (70) with pump means (72, 84) for pumping the liquid and connected firstly to the patient via a downstream tube (78) and secondly to coupling means (54). An application is performing perfusion prior to radiological examination using an X-ray or an NMR scanner.

31 Claims, 3 Drawing Sheets

CONTINUOUSLY OPERATING INFUSION DEVICE AND METHOD

The invention relates to an injection method and apparatus capable of operating continuously.

In certain medical applications or certain medical examinations, such as radiological scanning (using X-rays or nuclear magnetic resonance (NMR)), it is necessary to inject the patient.

In some cases the injection must be performed continuously on the same patient, and in other cases the apparatus must be quickly reusable so as to make it possible to pass very quickly from one patient to another, i.e. without any need to reinstall the entire injection apparatus. It is therefore desirable to optimize the time required for preparing injection between patients.

In addition, the injection liquid is sometimes expensive, so it is necessary to have apparatus suitable for limiting losses of liquid during injection, in particular when changing the bottle containing the liquid.

It would be even more advantageous to use all of the contents of an injection bottle over a plurality of patients and to inject each patient with the quantity of liquid that turns out to be necessary during the examination.

The various injection apparatuses that have been in use until now do not satisfy the conditions specified above: the quantity of substance provided has been that required for examination of one patient. In the event of this quantity turning out to be insufficient it has been impossible to add more substance without interrupting injection, and when the quantity has been excessive, the left over substance has had to be discarded because of the risk of contamination.

An object of the injection apparatus of the invention is to remedy the drawbacks of prior art apparatuses as mentioned above.

According to the invention, this object is achieved by the fact that the injection apparatus comprises two independent feed sources of at least one liquid to be injected into a patient via a tube, said injection apparatus comprising, for each feed source, interrupter means for interrupting the flow of the liquid and detection means for detecting that injection of the liquid contained in the feed source has terminated, said interrupter means being controlled by said detection means.

The following advantageous dispositions are also preferably adopted:

each feed source is an injection bottle, the injection apparatus further comprising: upstream injection apparatus constituted by a first feed tube, a second feed tube, and for each of the injection bottles, respective link means, each of the first and second feed tubes being connected by the link means to one of the injection bottles; and downstream injection apparatus comprising a downstream tube and pump means for pumping the liquid, said downstream tube connecting said pump means to the patient;

the upstream injection apparatus further comprises single coupling means secured to the first and second feeder tubes capable of being connected to the pump means;

the pump means comprise antireturn means preventing the liquid flowing in said downstream injection apparatus returning into said upstream injection apparatus; and some of the link means, on the one hand, the coupling means and the pump means, on the other hand, are interconnected by connection means that simultaneously perform fixing and establish liquid flow.

In another aspect, the invention provides a method in which changeover from one feed source to the other is performed automatically due to the fact that said means for detecting that injection of the liquid contained in the feed source has terminated cause the interrupter means for interrupting the flow of liquid from said feed source to close and also cause the interrupter means of the other feed source to open.

The invention will be better understood and secondary characteristics and advantages thereof will appear on reading the following description of an embodiment given by way of example.

Naturally the description and the drawings are given solely by way of non-limiting indication.

Reference is made to the accompanying drawings, in which.

Figure 1:
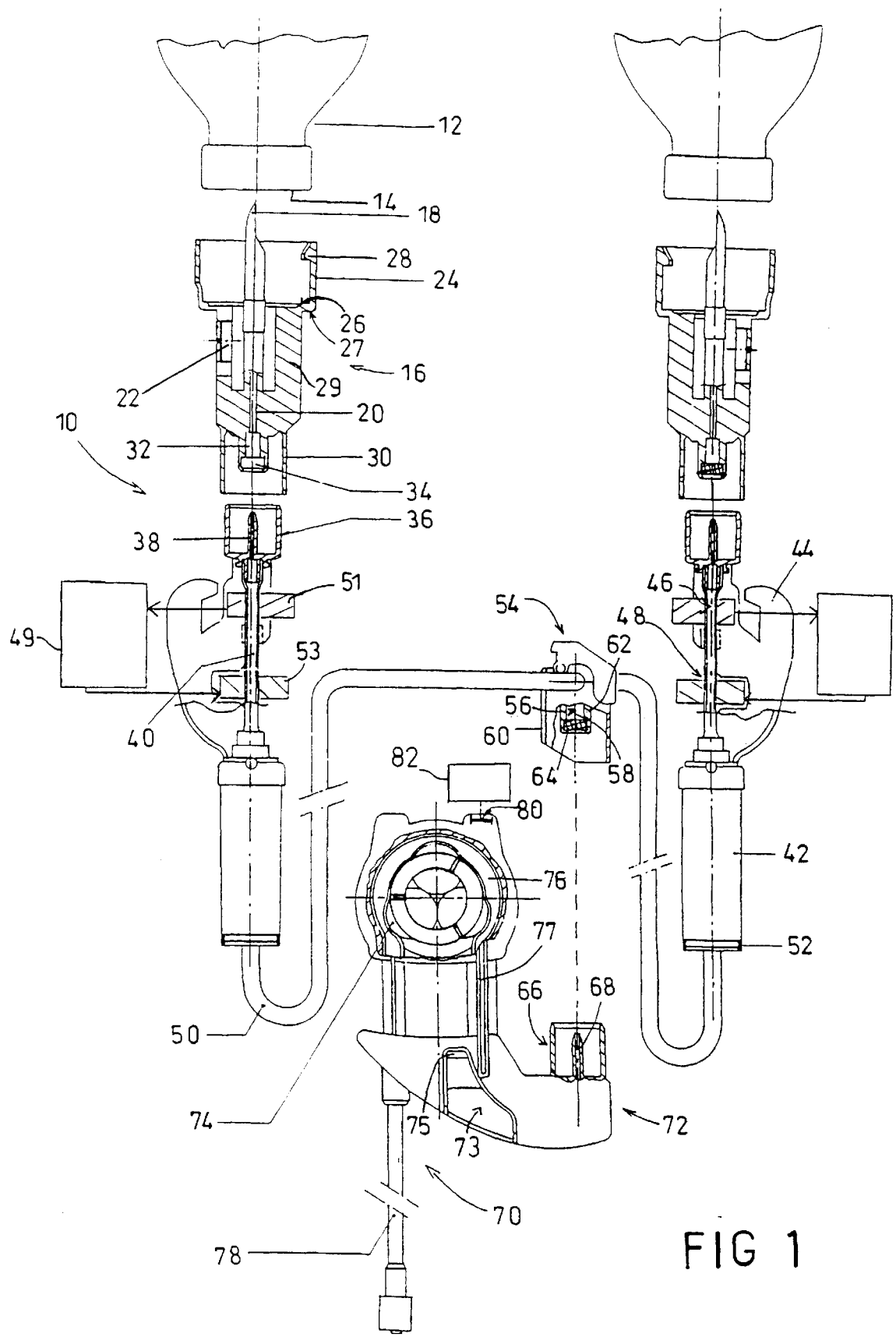
FIG. 1 is an exploded view in partial section showing the various parts to be interconnected of the injection apparatus of the invention.

As can be seen in FIG. 1, the injection apparatus of the invention is a two-bottle system.

In the figure, the detection and control means are not shown in detail, but they are represented diagrammatically and their operation is described below.

The flow circuit for the liquid that is to be perfused or injected into a patient includes a tee, i.e. two symmetrical upstream circuits, converging on a single downstream circuit connected to the patient.

The injection apparatus is described from upstream to downstream. Since the upstream apparatus has two absolutely identical series of elements, only the portion of the upstream apparatus as visible on the left of FIG. 1 is described, it being understood that symmetrical apparatus exists in the form of a right-hand portion of the upstream apparatus which comprises exactly the same elements as those described below.

The upstream injection apparatus 10 comprises firstly a bottle 12 containing the liquid substance that is to be injected into the patient. The bottle is closed by an elastic capsule 14 at the leading end of the bottle cap.

A piercing pin 16 constitutes means for perforating the injection bottle 12 since it enables the capsule 14 of the bottle 12 to be pierced and is designed to allow liquid to flow from the bottle 12 towards the elements that are downstream from the pin 16. For this purpose, the pin 16 has a hollow bevelled tip 18 extending the upstream end of an internal duct 20 passing axially right through the pin 16. The internal duct 20 is connected to air inlet means constituted by an air intake 22 enabling air to penetrate into the bottle 12 via the hollow tip 18 to allow the bottle 12 to empty its contents.

Advantageously, a portion of the pin surrounds its tip 18 in the form of a cylindrical side wall 24 of circular section having an inside diameter that is only slightly greater than the outside diameter of the cap of the bottle. This side wall 24 is extended radially inwards by a shoulder 26 which serves as an abutment element for the leading face of the cap of the bottle. Preferably, the side wall 24 has axial slots regularly distributed around its circumference and possesses an inwardly directed annular rim 28. The annular rim 28 forms a resilient rim designed to hold the rear of the bottle cap and prevent any involuntary axial separation movement between the pin and the bottle.

As can be seen in FIG. 1, the bottle 12 is upside-down, with its cap at the bottom, and the tip 18 projects axially beyond the annular rim 28 of the side wall 24.

Connection between the bottle 12 and the pin 16 is described below. The tip 18 is pushed into the capsule 14 of the bottle and the bottle and the pin are moved towards each other until the cap comes into abutment against the shoulder 26. As they move towards each other, the side wall 24 spreads out because of its slots, however once the cap is in abutment, the side wall returns to its initial shape because of the resilience made possible by the slots, so the annular rim 28 comes into abutment above the side zone of the rear face of the cap: the pin 16 and the bottle 12 are held together and the side wall 24 supports the bottle cap both axially and laterally.

The tip 18 provides axial guidance between the bottle 12 and the pin 16. The tip 18, the side wall 24, the shoulder 26, and the annular rim 28 constitute both axial and lateral support and also retaining means for the cap of the bottle 12, enabling the bottle 12 to be held vertically upside-down without any other fixing means. The position of the bottle 12 is thus fully determined by the pin 16.

The middle portion of the pin 16 constitutes the body 29 of the pin 16, said pin body 29 is preferably generally cylindrical in outside shape, of circular section, and extended upstream by an outer radial shoulder 27 enabling the side wall 24 to be coupled to the pin body 29.

The downstream portion of the pin 16 forms a cylindrical length 30 of circular section whose axis coincides with the axis of the internal duct 20. The internal duct 20 terminates downstream in a cylindrical wall 32 closed at its end by a membrane or septum of pre-slit latex 34. The cylindrical wall 32 is surrounded by the cylindrical length 30 which projects axially beyond the membrane 34.

The downstream portion of the pin 16 is coupled to a cylindrical rigid element 36 in the form of a circular section cup of outside diameter substantially equal to the inside diameter of the cylindrical length 30 so that coupling is achieved by axial sliding and sliding telescopic engagement with or without friction between the rigid element 36 and the downstream portion 30 of the pin 16. The bottom of the rigid element 36 constitutes an abutment for the downstream end of the cylindrical length 30 of the downstream portion of the pin 16. The rigid element 36 also has an axial hollow tip 38 surrounded by the vertical walls of the rigid element 36, said tip 38 penetrating into the pre-slit septum 34 and being partially contained in the downstream portion of the internal duct 20 of the pin when the rigid element 36 is coupled to the pin 16.

Figures 2, 3:
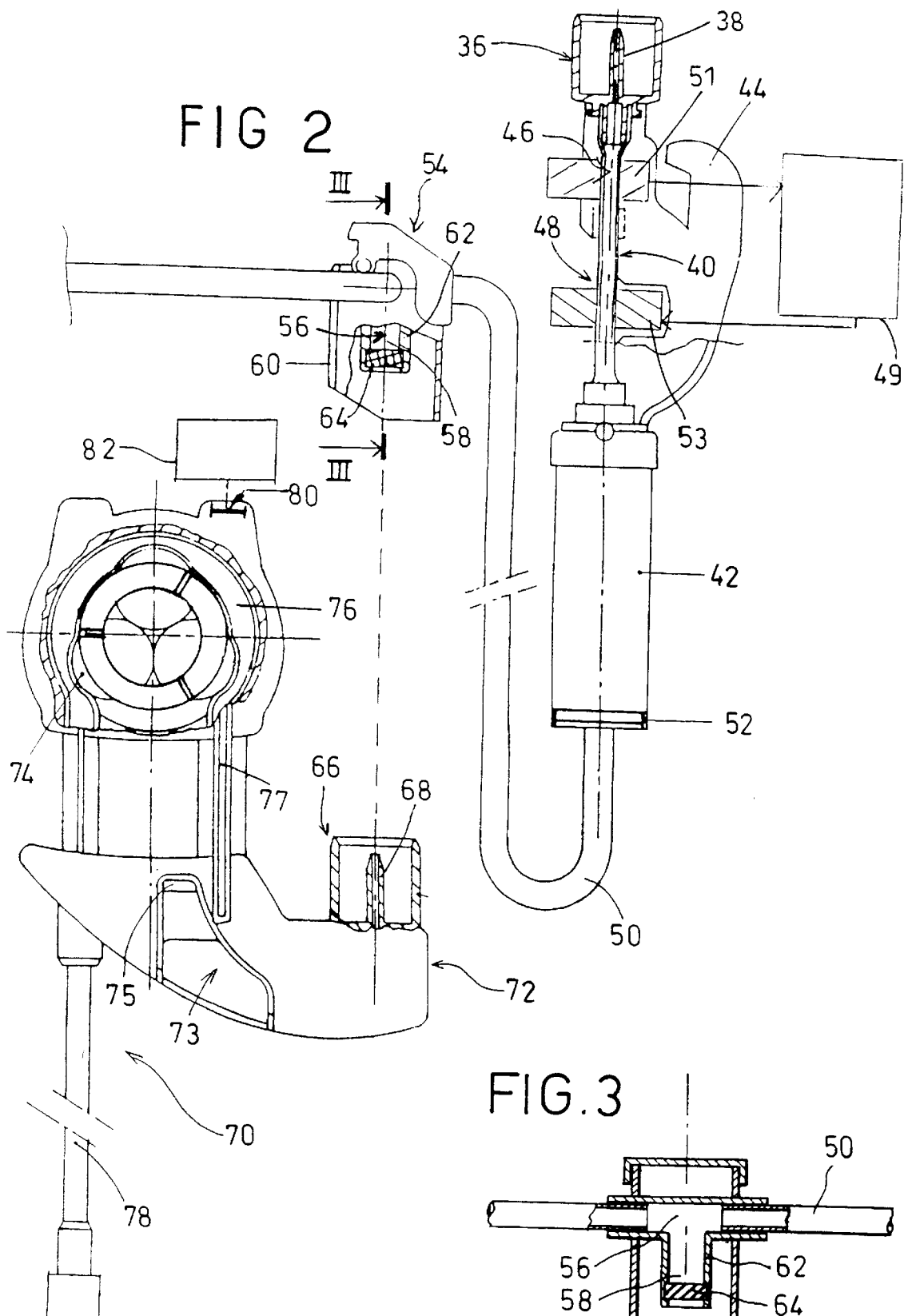
FIG. 2 is an enlarged view of certain parts of FIG. 1.
FIG. 3 is a section view of coupling means on line III—III in FIG. 2.

As shown in FIG. 2, a resilient flexible tube 40 is connected firstly to the downstream end of the hollow tip 38 of the rigid element 36 and secondly to the upstream portion of a drip chamber 42. The assembly constituted by the rigid element 36, the flexible tube 40, and the drip chamber 42 is held in alignment by a rigid ear-shaped support 44 which connects the downstream portion of the rigid element 36 to the upstream portion of the drip chamber 42, partially surrounding the flexible tube 40 so as to create an upstream length 46 of the flexible tube 40 and a downstream length 48 of the flexible tube 40 on either side of the length of flexible tube that is surrounded by the support 44.

The pin 16, the rigid element 36, the flexible tube 40, and the drip chamber 42 constitute link means connecting the bottle 12 to a feeder tube 50.

The means for detecting that injection of the liquid contained in the feed source or bottle 12 has terminated consist either in means for detecting that the feed source is empty, such as an air detector, or else in means for monitoring the quantity of liquid that is flowing, such as a flow meter that is capable of stopping the flow when the quantity of liquid that has flowed through corresponds to a preprogrammed determined value.

An air detector 51 is preferably positioned at the upstream length 46 of the flexible tube. This detector 51 can consist in any system for detecting that the flexible tube is not full of liquid but contains air due to a problem of liquid flow or to the fact that the bottle 12 is empty.

By way of example, the air detector 51 may be constituted by two piezoelectric sensors placed facing each other across the flexible tube 40 and in contact with the outside of the tube. One sensor acts as an ultrasound wave emitter and the other as a receiver of said wave after it has propagated through the flexible tube 40.

Depending on whether the flexible tube 40 is full of liquid or of air, the electrical signal emitted by the piezoelectric receiver is different.

The air detector 51 makes it possible, via a control unit 49, to control electrically means 53 for interrupting liquid flow and situated at the downstream length 48 of the flexible tube 40. These interrupter means 53 may close the flexible tube 40 by pinching it so as to close or open the flexible tube upstream from the drip chamber 42. By way of example, it is possible to use an electric clamp which is preferably electrically controlled by the air detector 51 via an electrical relay. Manual control may also be provided for controlling the liquid flow interrupter means 53: this is not provided to switch from one bottle to the other, since that is performed automatically as described below, but solely for use when changing one of the two bottles or when initially installing both bottles on the apparatus. In either case, it is then necessary to purge the feeder tubes 50 and/or the flexible tubes 40 of their air by filling them with liquid under manual control of the liquid flow interrupter means 53.

The drip tube 42 is a flexible and resilient transparent cylindrical tube of circular section and of diameter much greater than that of the flexible tube 40, with both ends thereof being closed by respective covers through which the flexible tube 40 opens out at the upstream end and the feeder tube 50 opens out at the downstream end.

The downstream end of the drip chamber 42 preferably carries a circular filter 52 which retains in the drip chamber any particles that might have penetrated into the perfusion apparatus: for example particles of rubber or particles of plastic coming from the capsule 14 of the bottle 12, from the membrane 34, or from the bevelled tip 18 of the pin 16. The filter 52 also serves as a splash plug when high flow rates (10 ml/s or higher) pass through the injection apparatus. It is possible to use a plastic filter having 25 μm openings.

The contents of the drip chamber 42 serves as a buffer supply and as a bubble trap, particularly when changing bottles as described below. The supply of liquid contained in the drip chamber 42 makes it possible to prevent air getting into the feeder tube 50 placed downstream from the drip chamber 42: if any air does penetrate into the feeder tube 50, it is then necessary to purge the entire upstream injection apparatus 10 of its air, and that would waste liquid.

The first feeder tube 50 and the second feeder 50 of the upstream apparatus 10 are securely united at coupling means 54 preferably in the form of a rigid element having a T-shaped internal duct 56, as can be seen in FIG. 3, providing the pair of upstream circuits with a single outlet 58. Each of the two inlet ends of the T-shaped internal duct 56 is secured to a respective one of the first and second feeder tubes 50.

The outlet portion of the rigid element 54 is very similar in structure to the downstream portion of the pin 16: a cylindrical length 60 of circular section surrounds the end of the outlet 58 of the internal duct 56 which is constituted by a cylindrical wall 62 closed at its end by a septum of pre-slit latex 64.

The septum 64 performs the same functions as the septum 34 of the pin 16: by opening it allows a perforator element in the form of a tip to be inserted and held in place, and when the tip is withdrawn, the septum recloses because of its elasticity, thereby guaranteeing that the circuit upstream from the septum is sealed. The septum 64 constitutes sealing means closing the third end of the internal duct 56 and designed to co-operate with the upstream end of pump means.

The outlet portion of the rigid element 54 is designed to be coupled to a cylindrical rigid element 66 having a hollow tip 68, of identical structure to the rigid element 36. The rigid element 66 is placed upstream from pump means 72 and is designed to co-operate with the rigid element 54 in the same manner as the rigid element 36 co-operates with the downstream portion of the pin 16. Thus, as for the septum 34 of the pin 16, the pre-slit septum 64 is designed to surround in elastic manner a hollow tip 68 situated at the upstream end of the pump means 72. Telescopic sliding engagement between the cylindrical length 60 and the rigid cylindrical element 66 enables them to be fixed together and causes the hollow tip 68 to penetrate through the septum 64. Nevertheless, sliding between the cylindrical portions of the rigid elements 66 and 54 is not necessarily by friction since these elements are also supported by a motor module 84.

The coupling means 54 also comprise closure means for partially closing the internal duct 56 enabling liquid to flow either from the two inlet ends of the internal duct 56 towards the outlet end 58 of the internal duct 56, or from one only of the two inlet ends towards the outlet end 58, the other inlet end being closed.

These partial closure means preferably consist in a three-port cock: three inlets and one outlet making it possible, depending on the rotary position of the cock relative to the coupling means 54, to use or not use each of the two liquid inlets. The cock is not designed to be manipulated while injection is taking place, but is used, for example, prior to an injection that will require only one bottle so as to disable one of the branches of the upstream injection apparatus 10.

Figure 4:
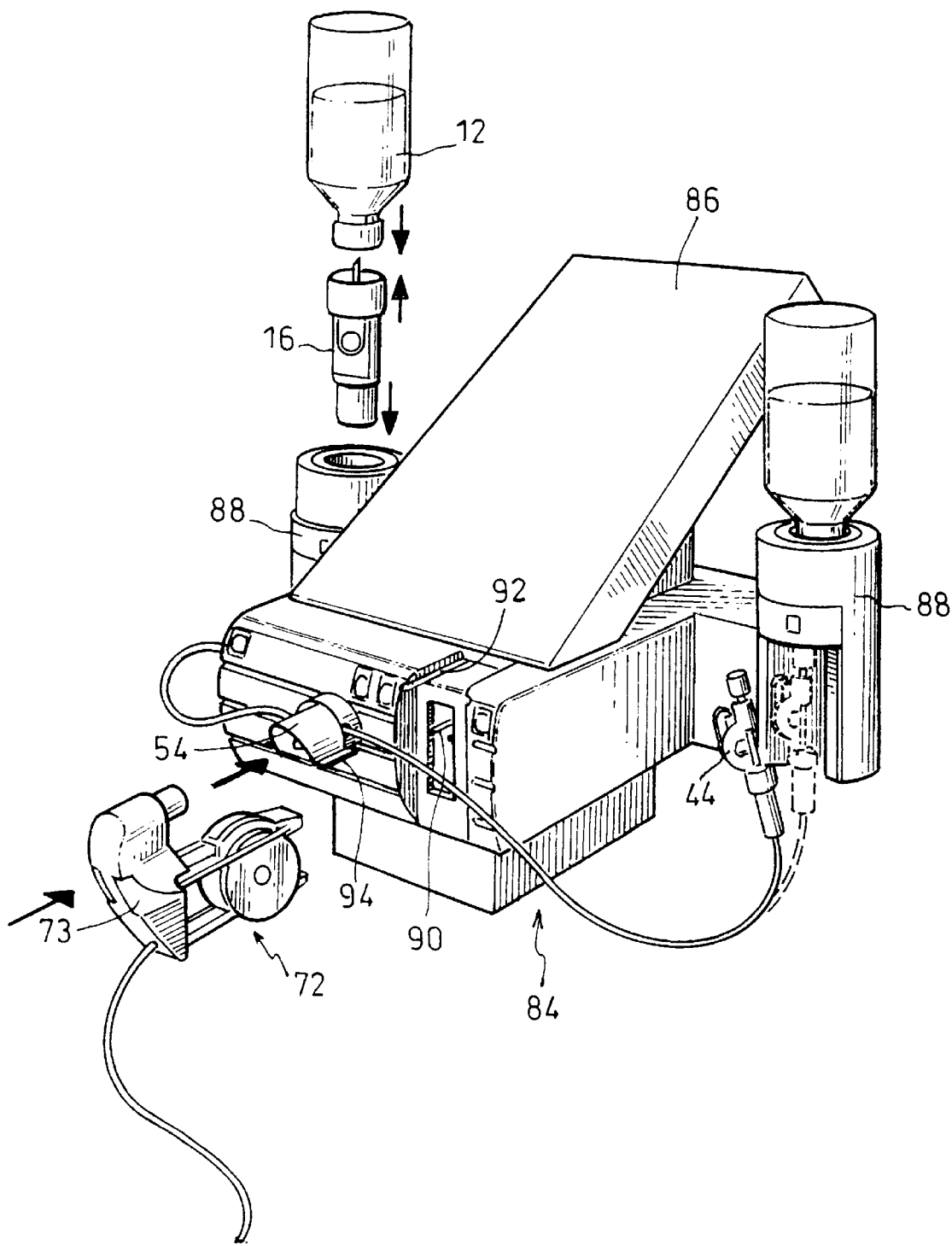
FIG. 4 is a diagram of the support element on which the parts of FIG. 1 are installed.

As shown diagrammatically in FIG. 4, the motor module 84 constitutes a pump body on which the other elements of the injection apparatus are placed.

The motor module 84 comprises firstly a pump motor with an outlet shaft, a control desk 86 for the injection apparatus, and a metal support 88 for the pin 16.

The support 88 is a circular section cylinder having an open-ended axial bore and a wide longitudinal slot which extends from one end of the support 88 over a fraction of its length and which opens into the bore. The axial bore has a top length of diameter that is greater than its bottom length; the transition zone between the top length and the bottom length forms an annular shoulder. The inside diameter of the bottom length corresponds to the outside diameter of the pin body 29, thereby enabling the bottom length of the support bore 88 to constitute an annular element surrounding the pin body 29 with a small amount of clearance so transverse movement of the pin is very limited, while axial movement thereof is limited by abutment between the annular shoulder of the support 88 and the outer annular shoulder 27 of the pin 16.

The pin body 29 and the outer annular shoulder 27 of the pin 16 constitute zones via which the pin 16 is held. When inserted in its support 88, the pin 16 is completely surrounded by the support 88. The bottle can be held in place via the open end of the top length of the support bore 88 and a fixing system enables the ear-shaped support 44 to be positioned in the longitudinal slot of the support 88 so that the tip 38 of the rigid element 36 passes through the septum 34 of the pin 16.

By means of the support 88, the bottle 12 remains upright and upside-down in spite of its weight, avoiding any movement of the pin 16 which can be much lighter than the bottle, particularly if the pin is made of plastic, for example.

The periphery of the pin body 29 preferably carries coding to enable the bottle 12 to be recognized by the motor module 84 of the pump means, specifying the type and the volume of liquid contained in the bottle 12.

By means of such coding, the injection apparatus of the invention recognizes the bottle when the assembly constituted by the pin 16 and the bottle 12 is inserted in the support 88. It is possible to design optical coding using a bar code reader, for example, or mechanical coding. Such mechanical coding is preferably constituted by a flexible membrane which detects the number and/or position of points disposed on the periphery of the pin body 29. The membrane can be located on the wall of the bottom length of the bore in the support 88.

The motor module 84 also has rails 90 enabling the peristaltic cassette 72 to slide in the motor module 84 so that when it is in abutment, the peristaltic cassette 72 is exactly in position for enabling the outlet shaft of the pump motor to drive the moving parts 74 of the peristaltic cassette 72 and for the tip 68 of the rigid element 66 to penetrate through the septum 64. To make that possible, the rigid element 54 is secured to a point on the motor module 84 provided for this purpose and including guide grooves 92. The grooves 92 constitute means for securing the rigid element 54 since they are complementary to lateral guide projections 94 included on the rigid element 54 on either side of an axis of symmetry. Close axial sliding between the lateral projections 94 and the grooves 92 provides accurate guidance with a final position that is determined by abutment.

The pump means 72, comprise a motor module 84 having rails 90 and at least one groove, and a peristaltic cassette 72 having longitudinal grooves 77 complementary to the rails 90 and at least one resilient tongue 73 whose free end carries a catch 75 for engaging in said groove to position the peristaltic cassette 72 accurately relative to the motor module 84.

The body of the peristaltic cassette 72 carries two resilient tongues 73 forming a clip which co-operates with the housing of the motor module 84 in which the cassette is inserted. When the peristaltic cassette 72 is inserted in the motor module 84, it is guided by the rails 90 and then the resilient tongues 73 curve towards the inside of the cassette because of the catches 75 which project outwards from the body of the cassette. Once the cassette 72 is fully inserted in the motor module 84, the catches 75 come into register with the grooves of the motor module, and because of the resilience of the tongues, the catches 75 become inserted into the grooves, thereby preventing any movement between the cassette 72 and the motor module 84. To release the cassette, it is necessary to press manually on the portions of the tongues 73 that remain outside the module so as to disengage the catches 75 from their grooves.

The rigid element 66 constitutes the upstream end of the downstream injection apparatus 70 which is described below with reference to FIG. 2.

The downstream injection apparatus 70 comprises pump means preferably made up of a peristaltic cassette 72 and an external motor module 84 whose outlet shaft rotates the moving parts 74 of the peristaltic cassette 72. A tube 76 passes through the peristaltic cassette 72 and has its upstream end connected to the rigid element 66.

The motor module 84 also has means in the form of sensors for detecting pressure and air. When the peristaltic cassette 72 is in position in the motor module 84, the outlet shaft and the detector means can move simultaneously, preferably horizontally, so that the outlet shaft co-operates with the moving parts 74 in order to enable the outlet shaft to drive the moving parts 74 and the detector means take up position around the downstream end portion of the tube 76 to verify the pressure and lack of air in the liquid going towards the patient.

The downstream end of the tube 76 of the peristaltic cassette 72 is connected to a downstream tube 78 which guides the liquid to the patient.

When the injection apparatus of the invention is in use, the pins 16 are inserted in their respective supports 88, the bottles 12 are connected to the corresponding pins 16, and the rigid elements 36 are connected to the corresponding pins 16, the rigid ear-shaped supports 44 being fixed to the supports 88 so that the flow of liquid is vertical between each bottle 12 and the corresponding drip chamber 42.

The peristaltic cassette 72 and the coupling means 54 are releasably engaged in the motor module so that the coupling means 54 can co-operate with the rigid element 66 as described above and so that the outlet shaft of the motor module can be positioned automatically to rotate the moving parts 74 of the peristaltic cassette 72.

The peristaltic cassette 72 and the motor module may be replaced by a peristaltic pump such as one of those described in French patent applications Nos. 2 383 333 and 2 644 212.

The entire circuit is then purged of air and filled with liquid prior to being connected to the patient and starting injection or perfusion by pumping the liquid from one of the two bottles 12, the flexible tube 40 of the other bottle being pinched by the interrupter means 53 to prevent liquid flowing.

When a bottle is empty, the air detector 51 causes the flow interrupter means 53 to close the flexible tube 40 corresponding to the empty bottle and the other bottle takes over in feeding the apparatus by automatically opening the interrupter means 53 corresponding to said other bottle.

It is thus possible to change the empty bottle by interrupting injection: it is necessary to replace the empty bottle with a new bottle and to fill the corresponding drip chamber by sucking in liquid by applying manual pressure to the flexible and resilient wall of the drip chamber 42, the flexible tube 40 connecting said drip chamber to a new bottle not being pinched by the interrupter means 53 for interrupting the flow of liquid while the other flexible tube must be closed.

This system makes it possible to inject up to twice the contents of one bottle into a single patient without interrupting injection: it suffices to pump from the second bottle while the first bottle is empty.

When changing patient, it is not necessary to change all of the elements described and shown, it suffices merely to change all of the elements in the downstream apparatus: the peristaltic cassette 72 and the downstream tube 78. The peristaltic cassette 72 preferably prevents any liquid that has penetrated into the downstream circuit 70 returning towards the upstream circuit 10 because the pump is occlusive: when the peristaltic cassette 72 is not pumping liquid from upstream to downstream, its rest position is such that the flexible tube 76 passing through it is pinched shut. This property enables the peristaltic cassette 72 to constitute means preventing any return of the liquid in the form of means that occlude the tube 76 included within the peristaltic cassette 72.

To prevent the peristaltic cassette 72 being reused with several patients, it is preferably provided with safety means comprising an automatically breakable plastic tongue 80 which breaks when the peristaltic cassette is inserted in the motor module.

Once the plastic tongue 80 has broken, further use of the peristaltic cassette 72 is made impossible by a detector system 82 for detecting the absence of the tongue 80.

This system includes electrical sensors which prevent the injection apparatus operating if the absence of the tongue 80 is detected when the peristaltic cassette 72 is inserted in the motor module, in an intermediate position preceding the stage in which the tongue 80 is broken.

Nevertheless, it is necessary for the cassette to be capable of being used once, even if the operator needs to reinsert the peristaltic cassette 72 in the motor module 84 after the tongue 80 has broken. For this purpose, it is possible to provide in the detection system 82 either a timer or else a monitoring system that authorizes single actual use of the injection apparatus after the tongue 80 has broken. If a timer is provided, then the operator is given a certain period in which to start injection after the tongue 80 has broken.

Timing starts when the tongue 80 breaks and while the period is being timed, it is possible to begin injection, whereas once the period has elapsed, it is impossible to perform injection.

Whatever the means used, the detection system 82 prevents the same peristaltic cassette 72 being used for a second injection.

It is also possible for each feed source or bottle 12 to provide a different liquid. This can make it possible to inject two different substances in succession during the same medical examination. One application is NMR radiological scanning in which one liquid is an active liquid known as a "contrast liquid" while the other liquid is an inert purging liquid, e.g. a solution of glucose or a physiological serum, for expelling into the patient any active liquid that remains in the downstream injection apparatus 70 once active liquid injection has terminated, i.e. when the active liquid bottle is empty, or when the total amount of active liquid that has passed through has reached a predetermined value. In this type of injection, the amount of active liquid that is injected is small and it is important to inject the major portion of the active liquid which remains in the pipework downstream of the interruption means 53 after the flexible tube 40 has been closed thereby: automatically switching over to the other bottle makes it possible for the purge liquid to entrain into the patient a portion of the active liquid corresponding to the active liquid contained in the downstream injection apparatus 70 at the time the tube 40 of the active liquid bottle was closed.

We claim:

1. Injection apparatus capable of operating continuously, comprising:

two independent injection bottle means containing at least one liquid to be injected into a patient;

a downstream injection assembly comprising a downstream tube and pump means for pumping the liquid, said pump means having a downstream end and an upstream end, said downstream tube connecting said pump means to said patient;

an upstream injection assembly including a first feeder tube, a second feeder tube, and a first and a second link means each comprising a flexible and resilient tube, said first and said second link means being connected to said injection bottle means and connected respectively to said first and second feeder tubes;

a single coupling means having a first inlet and a second inlet and one outlet connected to said upstream end of said pump means, said first and second feeder tubes being respectively connected to said first and second inlets of said single coupling means;

a first and a second interrupter means, operatively coupled to said upstream injection assembly, for interrupting flow of the liquid from the associated injection bottle means to said respective first and second feeder tubes;

a first and a second detection means, operatively coupled to said upstream injection assembly, each comprising an air detector for detecting termination of injection of the liquid contained in said associated injection bottle means; and control means operatively connected to said first and second detection means and said first and second interrupter means, said control means being arranged to control one of said first and second interrupter means to interrupt flow to one of said feeder tubes when one of said first and second detection means detects that injection of the liquid contained in the associated injection bottle means has terminated and said control means being arranged to control the other of said first and second interrupter means to open flow from the other of said injection bottle means in order to automatically changeover from said one injection bottle means to said other injection bottle means.

2. Injection apparatus according to claim 1, wherein at least one of said first and second detection means is means for detecting that said injection bottle means is empty.

3. Injection apparatus according to claim 1, wherein at least one of said first and second detection means is means for monitoring the quantity of liquid that has been passed.

4. Injection apparatus according to claim 1, wherein the pump means comprise antireturn means preventing the liquid flowing in said downstream injection apparatus from returning into said upstream injection apparatus.

5. Injection apparatus according to claim 4, wherein the pump means have a tube passing therethrough, and wherein the antireturn means include occlusion means for occluding the tube and included in said pump means, the occlusion means closing said tube when said pump means are not pumping.

6. Injection apparatus according to claim 1, wherein the coupling means comprise a T-shaped internal duct having two inlet ends secured to respective ones of the first and second feeder tubes and having a third outlet end closed by sealing means for co-operating with the upstream end of the pump means.

7. Injection apparatus according to claim 6, wherein the coupling means further comprise partial closure means for partially closing the internal duct, enabling liquid to flow either from both inlet ends towards the outlet end or from only one of the two inlet ends towards the outlet end while the other inlet end is closed.

8. Injection apparatus according to claim 6, including a hollow tip situated at the upstream end of the pump means, wherein the sealing means comprise a pre-slit septum for surrounding in elastic manner said hollow tip.

9. Injection apparatus according to claim 1, wherein at least one of said first and second link means comprises a perforation means for perforating the injection bottle means to enable liquid to flow from the bottle towards the downstream portion of the perforation means and a flexible and resilient tube.

10. Injection apparatus according to claim 9, wherein the perforation means includes a pin having a beveled hollow tip located upstream from and in communication with an internal duct and a pre-slit latex septum downstream from said internal duct.

11. Injection apparatus according to claim 10, wherein the pin further comprises air inlet means.

12. Injection apparatus according to claim 10, wherein the pin further possesses means for supporting and retaining a cap of the bottle enabling the bottle to be held vertically upside-down without further fixing means.

13. Injection apparatus according to claim 10, wherein the pin further possesses a cylindrical pin body of circular section that is extended upstream from an outer radial shoulder, and wherein the pin body is retained by an annular element for surrounding the pin body and coming into abutment against the outer shoulder.

14. Injection apparatus according to claim 9, including at least one drip chamber, wherein the flexible tube is disposed upstream from said drip chamber and comprises an upstream length and a downstream length, at least one of said first and second detection means for detecting that injection of the liquid contained in the feed source has terminated being located in register with said upstream length.

15. Injection apparatus according to claim 14, wherein at least one of said first and second interrupter means for interrupting the flow of liquid is located level with said downstream length.

16. Injection apparatus according to claim 9, comprising at least one connection means, interconnected to at least one of said first and second link means and interconnected to said upstream end of said pump means, including a cylindrical wall with one end closed by a septum and surrounded by a cylindrical length downstream from said perforation means and also a rigid cylindrical element having an axial hollow tip upstream from the flexible and resilient tube, and wherein a fixing means includes telescopic sliding engagement between the cylindrical length and the cylindrical rigid element, said engagement causing the hollow tip to penetrate through the septum.

17. Injection apparatus according to claim 1, wherein at least one of said first and second link means further includes a drip chamber disposed upstream from the feed tube and downstream from at least one of said first and second interrupter means for interrupting the flow of liquid.

18. Injection apparatus according to claim 17, wherein said drip chamber comprises a bubble trap.

19. Injection apparatus according to claim 17, wherein the drip chamber includes filter means.

20. Injection apparatus according to claim 17, wherein the drip chamber includes splash plug means.

21. Injection apparatus according to claim 1, wherein said pump means further comprise safety means which prevent the pump means from being reused.

22. Injection apparatus according to claim 21, wherein the safety means comprise an automatically breakable element and a detector system for detecting the absence of the automatically breakable element.

23. Injection apparatus according to claim 22, wherein at least one of said first and second detection means includes a timer whose starting point occurs upon breaking of the automatically breakable element and which allows injection to be started during its timer period.

24. Injection apparatus according to claim 1, wherein at least one of said first and second link means is interconnected by connection means that simultaneously perform fixing and establish liquid flow, and wherein said outlet of said coupling means and said upstream end of said pump means are interconnected by said connection means.

25. Injection apparatus according to claim 1, including at least one connection means that comprises a cylindrical wall disposed in the coupling means and having an end closed by a septum and surrounded by a cylindrical length, and wherein the pump means further comprise a cylindrical rigid element having a hollow tip and wherein a fixing means includes telescopic sliding engagement between the cylindrical length and the cylindrical rigid element, said engagement causing the hollow tip to penetrate through the septum.

26. Injection apparatus according to claim 1, wherein the periphery of the pin body carries coding to enable the pump means to recognize the bottle, including a type and volume of liquid contained in said bottle.

27. Injection apparatus according to claim 1, wherein the pump means comprise a motor module including rails and at least one groove, and a peristaltic cassette having longitudinal grooves complementary to the rails and at least one resilient tongue whose free end carries a catch for inserting into said groove to ensure that the peristaltic cassette is accurately positioned relative to the motor module.

28. Injection according to claim 27, wherein the motor module further includes an outlet shaft and detector means for detecting pressure and air, wherein the peristaltic cassette further includes moving parts and a tube, and wherein when the peristaltic cassette is in position in the motor module, the outlet shaft and the detector means are capable of moving simultaneously so that the outlet shaft co-operates with the moving parts and the detector means take up position around the downstream end portion of the tube.

29. Injection according to claim 1, wherein at least one of said first and second interrupter means comprises pinch means for pinching said flexible and resilient tube to interrupt the flow of the liquid from the associated injection bottle means to the associated feeder tube.

30. An injection method capable of operating continuously, comprising:

providing two independent injection bottle means containing at least one liquid;

providing a downstream injection assembly comprising a downstream tube and pump means for pumping the liquid, said pump means having a downstream end and an upstream end, said downstream tube connecting said pump means to said patient;

providing an upstream injection assembly including a first feeder tube, a second feeder tube, and a first and a second link means each comprising a flexible and resilient tube, said first and said second link means being connected to said injection bottle means and connected respectively to said first and second feeder tubes;

providing a single coupling means having a first inlet and a second inlet and one outlet connected to said upstream end of said pump means, said first and second feeder tubes being respectively connected to said first and second inlets of said single coupling means;

providing a first and a second interrupter means, operatively coupled to said upstream injection assembly, for interrupting flow of the liquid from the associated injection bottle means to said respective first and second feeder tube;

providing a first and a second detection means, operatively coupled to said upstream injection assembly, each comprising an air detector for detecting termination of injection of the liquid contained in said associated injection bottle means;

providing control means operatively connected to said first and second detection means and said first and second interrupter means;

injecting into a patient the liquid from one of said injection bottle means;

detecting termination of injection of the liquid contained in said one injection bottle means;

interrupting, by one of said first and second interrupter means controlled by said control means, flow to said feeder tube being in communication with said one injection bottle means; and opening flow, by another of said first and second interrupter means controlled by said control means, from the other of said injection bottle means to the associated feeder tube in order to automatically changeover from said one injection bottle means to said other injection bottle means.

31. The injection method according to claim 30 further including another liquid to be injected, wherein one of the liquids is an active liquid, the other liquid being a purge liquid and the method includes flushing into the patient any active liquid that remains in the downstream injection apparatus when injection of the active liquid has terminated.

* * * * *